US006887706B2

(12) United States Patent
Zhang et al.

(10) Patent No.: US 6,887,706 B2
(45) Date of Patent: May 3, 2005

(54) METHOD OF IN VITRO DIFFERENTIATION OF TRANSPLANTABLE NEURAL PRECURSOR CELLS FROM PRIMATE EMBRYONIC STEM CELLS

(75) Inventors: Su-Chun Zhang, Middleton, WI (US); James A. Thomson, Madison, WI (US); Ian David Duncan, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 09/970,382

(22) Filed: Oct. 3, 2001

(65) Prior Publication Data

US 2003/0068819 A1 Apr. 10, 2003

(51) Int. Cl.[7] .............................. C12N 5/00; C12N 5/02; C12N 5/06; C12N 5/08
(52) U.S. Cl. ....................... 435/377; 435/325; 435/363; 435/366
(58) Field of Search ................................. 435/325, 363, 435/366, 368, 377–378

(56) References Cited

U.S. PATENT DOCUMENTS

| 5,843,780 | A | 12/1998 | Thomson et al. |
|---|---|---|---|
| 6,200,806 | B1 | 3/2001 | Thomson et al. |
| 6,251,669 | B1 * | 6/2001 | Luskin ........................ 435/375 |
| 6,468,794 | B1 | 10/2002 | Uchida et al. |
| 2002/0028510 | A1 * | 3/2002 | Sanberg et al. ............. 435/368 |
| 2002/0068045 | A1 | 6/2002 | Reubinoff et al. |
| 2002/0114788 | A1 | 8/2002 | Isacson et al. |

FOREIGN PATENT DOCUMENTS

| WO | WO 97/47734 A1 | 12/1997 |
|---|---|---|
| WO | WO 99/20740 A2 | 4/1999 |
| WO | WO 99/20741 A1 | 4/1999 |
| WO | WO 01/51616 A2 | 7/2001 |
| WO | WO 01/81549 A2 | 11/2001 |
| WO | WO 01/83715 A2 | 11/2001 |
| WO | WO 01/88104 A2 | 11/2001 |

OTHER PUBLICATIONS

Brustle et al. In vitro–generated neural precursors participate in mammalian brain development. Proc. Natl. Acad. Sci. 94:14809–14814, 1997.*
Kawata et al. Neural rosette formation within in vitro spheroids of a clonal human tetracarcinoma cell line, PA–1/NR: Role of extracellular matrix components in the morphogenesis. Cancer Res. 51:2655–2669, 1991.*
Keystone Symposium on Pluripotent Stem Cells, Feb. 6, 2001 (Poster), Su–Chun Zhang, James A. Thomson, Ian David Duncan, Marius Wernig and Oliver Brustle.
M. K. Carpenter, et al., "Enrichment of Neurons and Neural Precursors from Human Embryonic Stem Cells," Exp. Neurol. 172:383–397, 2001.

* cited by examiner

Primary Examiner—David Gozo
Assistant Examiner—Quang Nguyen
(74) Attorney, Agent, or Firm—Quarles & Brady LLP

(57) ABSTRACT

A method of differentiating embryonic stem cells into neural precursor cells is disclosed. In one embodiment the method comprises the steps of (a) obtaining an embryonic stem cell culture, (b) propagating the stem cells, (c) forming embryoid bodies from the stem cells, and (d) culturing the embryoid bodies in a medium containing an effective amount of fibroblast growth factor 2, wherein neural precursor cells will be generated and isolated.

1 Claim, 3 Drawing Sheets

Figure 1:
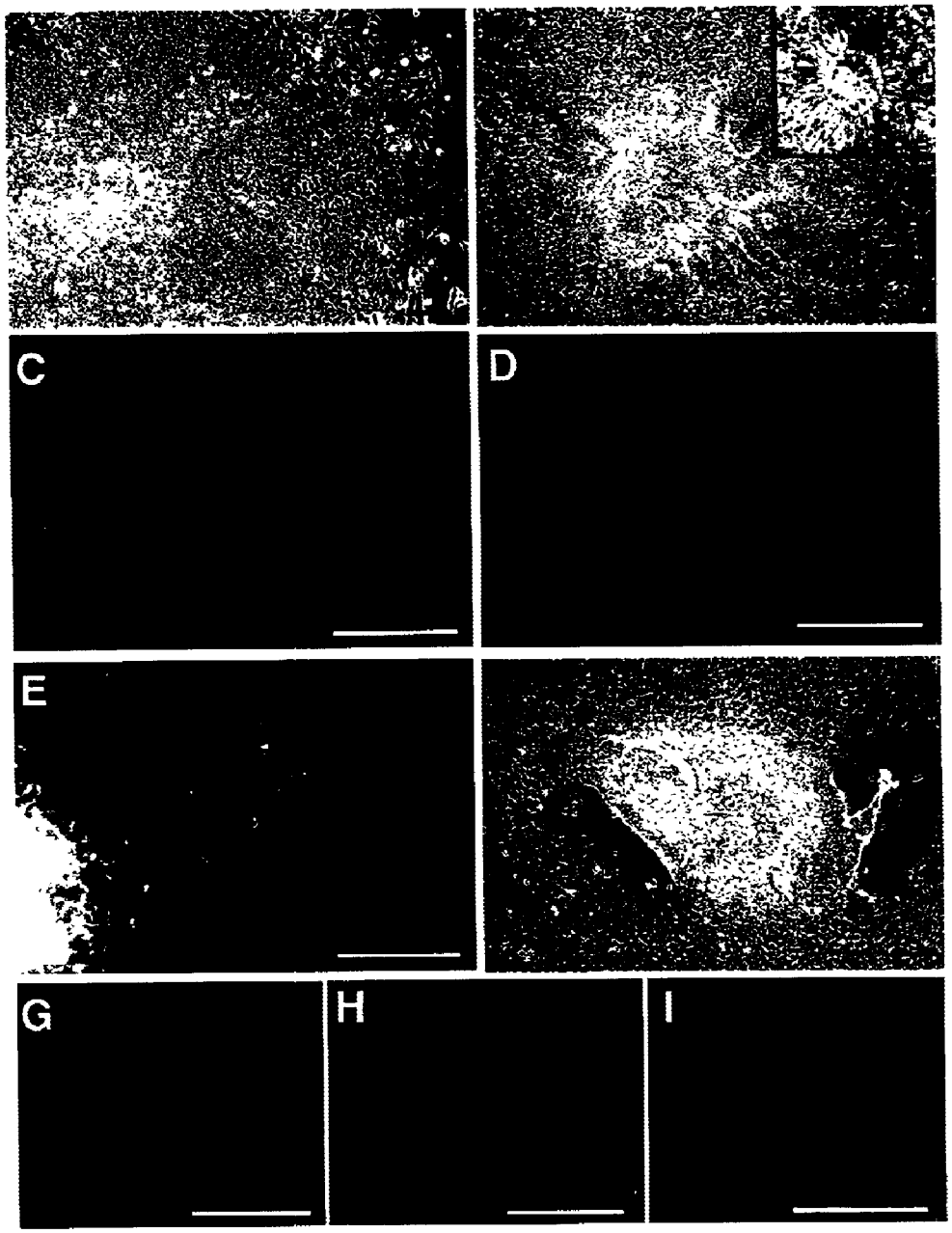

METHOD OF IN VITRO DIFFERENTIATION OF TRANSPLANTABLE NEURAL PRECURSOR CELLS FROM PRIMATE EMBRYONIC STEM CELLS

CROSS-REFERENCE TO RELATED APPLICATION

STATEMENT REGARDING FEDERALLY SPONSORED RESEARCH OR DEVELOPMENT

This invention was made with no United States government support.

BACKGROUND OF THE INVENTION

Human embryonic stem (ES) cells are pluripotent cells derived from the inner cell mass of preimplantation embryos (1). Similar to mouse ES cells, they can be expanded to large numbers while maintaining their potential to differentiate into various somatic cell types of all three germ layers (1–4). The in vitro differentiation of ES cells provides new perspectives for studying the cellular and molecular mechanisms of early development and the generation of donor cells for transplantation therapies. Indeed, mouse ES cells have been found to differentiate in vitro to many clinically relevant cell types, including hematopoietic cells (5), cardiomyocytes (6), insulin-secreting cells (7), and neurons and glia (8–11). Following transplantation into the rodent central nervous system (CNS), ES cell-derived neural precursors have been shown to integrate into the host tissue and, in some cases, yield functional improvement (13). A clinical application of human ES cells would require the generation of highly purified donor cells for specific tissues and organs.

Needed in the art is a simple, yet efficient, strategy for the isolation of transplantable neural precursors from differentiating human ES cell cultures.

SUMMARY OF THE INVENTION

The remarkable developmental potential and replicative capacity of primate embryonic stem (ES) cells promise an almost unlimited supply of specific cell types for transplantation therapies. Here we disclose the in vitro differentiation and enrichment of primate neural precursor cells from ES cells. In one embodiment of the present invention, after aggregation to embryoid bodies (EBs), differentiating primate ES cells form neural tube-like structures in the presence of an effective amount of fibroblast growth factor-2 (FGF2).

In another embodiment, neural precursors within these formations are isolated by selective enzymatic digestion and, preferably, further purified based on differential adhesion. Following withdrawal of FGF2, the cells may be differentiated into neurons, astrocytes and oligodendrocytes.

It is an object of the present invention to provide primate neural precursor cells, preferably transplantable.

Other objects, advantages and features of the present invention will become apparent after one of skill in the art has reviewed the specification, claims and drawings.

DETAILED DESCRIPTION OF THE SEVERAL VIEWS OF THE DRAWINGS

FIGS. 1A–I. Differentiation and isolation of neural precursors from ES cells. (FIG. 1A) An attached EB grown in the presence of FGF2 for 5 days shows flattened cells at the periphery and small elongated cells congregated in the center. (FIG. 1B) By 7 days, many rosette formations (arrows) appeared in the differentiating EB center. The up-right inset is the 1-μm section of the rosette stained with toluidine blue, showing columnar cells arranged in a tubular structure. Bar=20 μm. (FIGS. 1C–E) Cells in a cluster of rosettes (low left) and a small forming rosette (center) are positive for nestin (FIG. 1C) and Musashi-1 (FIG. 1D) whereas the surrounding flat cells are negative. (FIG. 1E) A combined image of FIG. 1C and FIG. 1D with all cell nuclei labeled with DAPI. (FIG. 1F) After treatment with dispase for 20 minutes, the rosette formations retracted whereas the surrounding flat cells remained attached. (FIGS. 1G–I) Isolated cells are positively stained for nestin in a filamentous pattern (FIG. 1G), Musashi-1 in cytoplasm (FIG. 1H), and PSA-NCAM mainly on membrane (FIG. 1I). All nuclei are stained with DAPI. Bar=100 μm.

Figure 2:
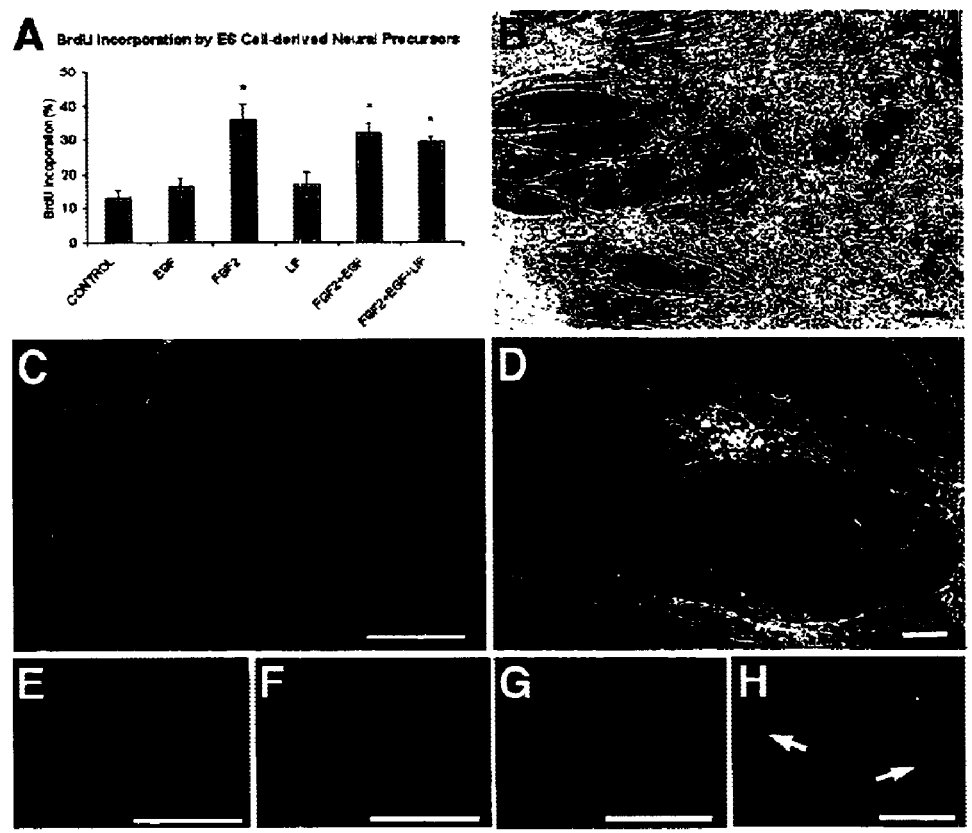

FIGS. 2A–G. Characterization of ES cell-derived neural precursors in vitro. (FIG. 2A) BrdU incorporation by dissociated ES cell-derived neural precursors is elevated in the presence of FGF2 (20 ng/ml) but not with EGF (20 ng/ml) or LIF (5 ng/ml). This is representative data from one of 3 replicate experiments. * indicates difference between the experimental group and the control group ($p<0.01$, $n=4$, student t-test). (FIG. 2B) Differentiation of a cluster of ES cell-derived neural precursors for 3 weeks shows neurite bundles with cells migrating along them. (FIG. 2C) Immunostaining after 3 weeks of differentiation indicates that the majority of cells are $\beta_{III}$-tubulin+ neurons (red) and that only a few cells are GFAP+ astrocytes (green). (FIG. 2D) After 45 days of differentiation, many more GFAP+ astrocytes (green) appear along with NF200+ neurites (red, yellowish due to overlapping with green GFAP). (FIGS. 2E–G) ES cell-derived neurons with various morphologies express distinct neurotransmitters such as glutamate (FIG. 2E), GABA (FIG. 2F) and the enzyme tyrosine hydroxylase (FIG. 2G). O4+ oligodendrocytes (arrows) are observed after 2 weeks of differentiation in a glial differentiation medium. Bar=100 μm.

FIGS. 3A–K. Incorporation and differentiation of ES cell-derived neural precursors in vivo. Grafted cells are detected by in situ hybridization with a probe to the human alu-repeat element (FIGS. 3A–E, G) or an antibody to a human-specific nuclear antigen (FIG. 3F). (FIG. 3A) Individual donor cells in the host cortex of an 8-week-old recipient (arrows). (FIG. 3B) Extensive incorporation of ES cell-derived neural precursors in the hippocampal formation. Cells hybridized with the human alu probe are labeled with red dots (pseudo-colored). (FIG. 3C) Incorporated human cells in the vicinity of the hippocampal pyramidal layer at P14. (FIG. 3D) ES cell-derived cells in the septum of a 4-week-old recipient mouse. (FIG. 3E) High power view of an individual donor cell in the hypothalamus. Note the seamless integration between adjacent unlabeled host cells. (FIG. 3F) Donor cells in the striatum of a 4-week-old host, detected with an antibody to a human-specific nuclear antigen. (FIG. 3G) Extensive migration of transplanted cells from the aqueduct into the dorsal midbrain. (FIG. 3H) Human ES cell-derived neuron in the cortex of a 2-week-old host, exhibiting a polar morphology and long processes. The cell is double labeled with antibodies to a human-specific nuclear marker (green) and $\beta_{III}$-tubulin (red). (FIG. 3I) Network of donor-derived axons in the fimbria of the hippocampus, identified with an antibody to human neurofilament. (FIG. 3J) Donor-derived multipolar neuron, double labeled with an antibody recognizing the a and b isoforms of MAP2. (FIG. 3K) ES cell-derived astrocyte in the cortex of a 4-week-old animal, double labeled with the human nuclear marker (green) and an antibody to GFAP (red). Note that all the double labelings are confocal images and are confirmed by single optical cuts. Bars: FIG. 3A, FIG. 3B, FIG. 3G 200 μm; FIG. 3C, FIG. 3D 100 μm; FIG. 3E, FIG. 3F, FIGS. 3H–K 10 μm.

DETAILED DESCRIPTION OF THE INVENTION

The present invention is a method of differentiating primate ES cells (preferably human ES cells) into neural precursors, preferably transplantable neural precursors suitable for nervous system repair. In a preferred embodiment, a primate ES cell line, preferably a human ES cell line, is first obtained and propagated. One may obtain an ES cell line as described in Thomson, J. A., et al., *Science* 282:1145–1147 (1998) and U.S. Pat. Nos. 5,843,780 and 6,200,806 or by other methods suitable to obtain a ES cell line with normal karyotypes and the ability to proliferate in an undifferentiated state after continuous culture for at least eleven months and preferably twelve months. The embryonic stem cell line will also retain the ability, throughout the culture, to form trophoblasts and to differentiate into tissue derived from all three embryonic germ layers (endoderm, mesoderm and ectoderm).

The cells are then cultured. In a preferred embodiment of the present invention, the cells are propagated on a feeder layer of irradiated mammalian, preferably mouse, embryonic fibroblasts, preferably as disclosed below and in Thomson, J. A., et al., *Science* 282:1145–1147 (1998) and U.S. Pat. Nos. 5,843,780 and 6,200,806. We envision that the cells may be propagated without feeder cell layers.

The ES cell colonies are typically removed intact from adherent cultures by treatment with dispase and grown in a suspension as free-floating ES cell aggregates called embryoid bodies (EBs), preferably for four days as described below.

The EBs are then cultured in medium containing fibroblast growth factor 2 (FGF2). The preferable components of the medium are as described below. However, many other medium components are suitable. A suitable medium is any medium used for growing neural cells. References 8–11, 14, 15, and 18–20 use the same or similar mediums. A preferred range of FGF2 is between 10–20 ng/ml.

After approximately five days of culture in the medium, the plated EBs will generate an outgrowth of flattened cells and by seven days the center small elongated cells will generate rosette formations such as seen in FIG. 1B. These formations resemble the early neural tube (insert of FIG. 1B). One may confirm the presence of neural precursors by morphology or by morphology or by immunofluorescence analysis using neural marker antigens such as Nestin and Musashi I, as described below. Preferably, the neural precursors comprise at least 72%, and most preferably at least 84%, of the total cells.

One may wish to further isolate the neural tube-like rosettes, preferably by differential enzymatic treatment and adhesion, as described below in the Examples. In brief, treatment with dispase will lead to the preferential detachment of the central neuroepithelial islands. To separate the clusters of rosette cells from the surrounding flat cells, the differentiating EBs cultured for 8–10 days are preferably incubated with 0.1–0.2 mg/ml dispase (Gibco BRL, Lifetechnologies, Rockville, Md.) at 37° C. for 15–20 minutes. The rosette clumps retract whereas the surrounding flat cells remain adherent. At this point, the rosette clumps may be dislodged by swaying the flask, which leaves the flat cells adherent. The clumps are pelleted, gently triturated with a 5 ml pipette and plated into a culture flask for 30 minutes to allow the contaminating individual cells to adhere. The floating rosette clumps are then transferred to a new flask, preferably coated with poly-(2-hydroxyethyl-methacrylate) to prohibit attachment, and cultured in a medium used for human neural precursors with the presence of FGF2 (typically 20 ng/ml). As described below in the Examples, treatment with dispase followed by differential adhesion will yield a highly enriched population of neural precursor cells, typically at least 90% and most preferably at least 96%. Additionally, one may use other methods, such as immune separation using an antibody to PSA-NCAM, to separate the neural precursor cells.

The Examples below demonstrate the human ES cell-derived neural precursors can generate all three CNS cell-types in vitro.

The table below is a flow chart of various aspects of the present invention:

TABLE 1

Characterization of the Neural Precursor Cells in vitro and in vivo

| | |
|---|---|
| ES cells | Treatment with dispase and cultured in free-floating condition with ES medium without FGF2 for 4 days. |
| ↓ | |
| Embryoid Bodies | Adherent culture in a chemically defined medium containing FGF2 for 7–9 days. |
| ↓ | |
| Differentiation to Neural tube-like structures | These are unique structures representative of neural epithelial cells as defined by histology and immunohistochemistry. Neural precursor cells typically comprise at least 72~84% of the total cells. |
| ↓ | |
| Isolation of Neural Precursor Cells with Dispase Treatment | Treatment with dispase followed by differential adhesion yields a highly enriched population of neural precursor cells (preferably at least 95%). |

In another embodiment, the present invention is a cell population comprising at least 72%, and preferably 84%, neural precursor cells. These neural precursor cells can be defined by being nestin and musashi I positive. FIG. 1B illustrates the rosette formation characterizing these cells. By rosette formation, we mean that cells are columnar in shape and are arranged in a tubular (rosette) structure, resembling the neural tube (developing brain) in the body. The columnar cell morphology and tubular structures are shown in the insert of FIG. 1B.

In another embodiment, the present invention is a cell population of at least 90% and preferably at least 96% neural precursor cells. One would preferably obtain these cells after differential enzymatic treatment and adhesion, as described below in the Examples.

EXAMPLES

Results

Human ES cells differentiate to form neural tube-like structures in the presence of FGF2. Human ES cell lines, H1, H9 and a clonal line derived from H9, H9.2 (4) were propagated on a feeder layer of irradiated mouse embryonic fibroblasts (1). To initiate differentiation, ES cell colonies were detached and grown in suspension as embryoid bodies (EBs) for 4 days. The EBs were then cultured in a tissue culture treated flask in a chemically defined medium (14, 15) containing fibroblast growth factor 2 (FGF2). FGF2 was obtained from Peprotech, Inc., Rocky Hill, N.J. After 5 days of culture in FGF2, the plated EBs had generated an outgrowth of flattened cells. At the same time, an increasing number of small elongated cells was noted in the center of the differentiating EBs (FIG. 1A). By 7 days in the defined medium, the central, small, elongated cells had generated rosette formations (FIG. 1B) resembling the early neural tube as shown by toluidine blue-stained sections (inset in FIG. 1B). Immunofluorescence analyses revealed that the expression of neural marker antigens nestin and Musashi-1 (16, 17), was largely restricted to cells in the rosettes but not the flat cells in the periphery of the differentiating EBs (FIGS. 1C–E). Undifferentiated ES cells were immunonegative for these markers. The formation of neural tube-like structures was noted in the majority of EBs in the presence of FGF2 (94% of the total 350 EBs from H9 and H9.2 lines, 3 separate experiments). In the absence of FGF2, no well organized rosettes were observed.

Neural tube-like rosettes can be isolated by differential enzymatic treatment and adhesion. With continued exposure to FGF2, the columnar rosette cells expanded and formed multiple layers. They frequently made up most of the EB and were sharply demarcated from the surrounding flat cells. Treatment with dispase led to the preferential detachment of the central neuroepithelial islands, leaving the surrounding cells largely adherent (FIG. 1F). Contaminating single cells were separated by short-term adhesion to cell culture dishes. Cell counts performed immediately after this isolation and enrichment procedure showed that cells associated with the isolated neuroepithelial clusters made up 72–84% of the cells in the differentiated EB cultures. Immunocytochemical analyses showed that 96±0.6% of the isolated rosette cells were positively stained for nestin based on 13,324 cells examined in 4 separate experiments. The vast majority of these cells were also positive for Musashi-1 and PSA-NCAM (FIGS. 1G, H, I).

Human ES cell-derived neural precursors generate all three CNS cell types in vitro. The isolated neural precursors were expanded as free-floating cell aggregates in a suspension culture, similar to "neurosphere" cultures derived from human fetal brain tissues (14, 18–20). BrdU incorporation studies revealed that stimulation of precursor cell proliferation was dependent on FGF2 and could not be elicited by either EGF or LIF alone. Furthermore, no additive or synergistic effects were observed when FGF2 was combined with EGF and/or LIF (FIG. 2A).

In vitro differentiation of the ES cell-derived neural precursors was induced by withdrawal of FGF2 and plating on ornithine and laminin substrate. Within a few days, individual cells and numerous growth cones grew out from the spheres, giving a star burst appearance. By 7–10 days after plating, processes emanating from the spheres had formed prominent fiber bundles. Frequently, small migrating cells were seen in close association with the fibers (FIG. 2B). Immunofluorescence analyses of the differentiated cultures revealed that the vast majority of cells in the outgrowth areas expressed neuronal markers MAP2ab and $\beta_{III}$-tubulin (FIG. 2C). Expression of low molecular weight neurofilament (NF) and high molecular weight NF was observed by 7–10 and 10–14 days after plating, respectively (FIG. 2D). Antibodies to various neurotransmitters were used to further characterize the ES cell-derived neurons. While the majority of the neurons exhibited a glutamatergic phenotype (FIG. 2E), a smaller proportion was labeled with an antibody to GABA. Frequently, these neurons showed a polar morphology (FIG. 2F). A small number of neurons were found to express TH (FIG. 2G), the rate-limiting enzyme for dopamine synthesis. GFAP+ astrocytes were rarely found within the first 2 weeks after growth factor withdrawal (FIG. 2C), but became more frequent after prolonged in vitro differentiation. By 4 weeks, they had formed an extensive layer underneath the differentiated neurons (FIG. 2D). While oligodendrocytes were not observed under standard culture conditions, a few O4-immunoreactive cells with typical oligodendrocyte morphology were observed when the cells were cultured in the presence of platelet-derived growth factor A (14) for longer than 2 weeks (FIG. 2H). Thus, ES cell-derived neural precursors generate all three major cell types of the CNS.

Human ES cell-derived neural precursors migrate, incorporate, and differentiate in vivo. To assess the differentiation of human ES cell-derived neural precursors in vivo, we grafted them into the lateral ventricles of newborn mice (21). The transplanted cells formed clusters in various regions of the ventricular system and incorporated in large numbers into a variety of host brain regions. Of 22 brains analyzed between 1 and 4 weeks after transplantation, intraventricular clusters and incorporated cells were found in 19 and 18 recipient brains, respectively. Individual animals analyzed after longer time periods showed that grafted cells were detectable for at least 8 weeks post transplantation. Cells within the clusters showed strong immunoreactivity to antibodies against nestin, $\beta_{III}$-tubulin and MAP2ab. Only a few cells in the aggregates expressed GFAP. Alkaline phosphatase and cytokeratine, markers typically expressed in undifferentiated ES cells and non-neural epithelia, were not detected within the clusters. No teratoma formation was observed.

Figure 3:
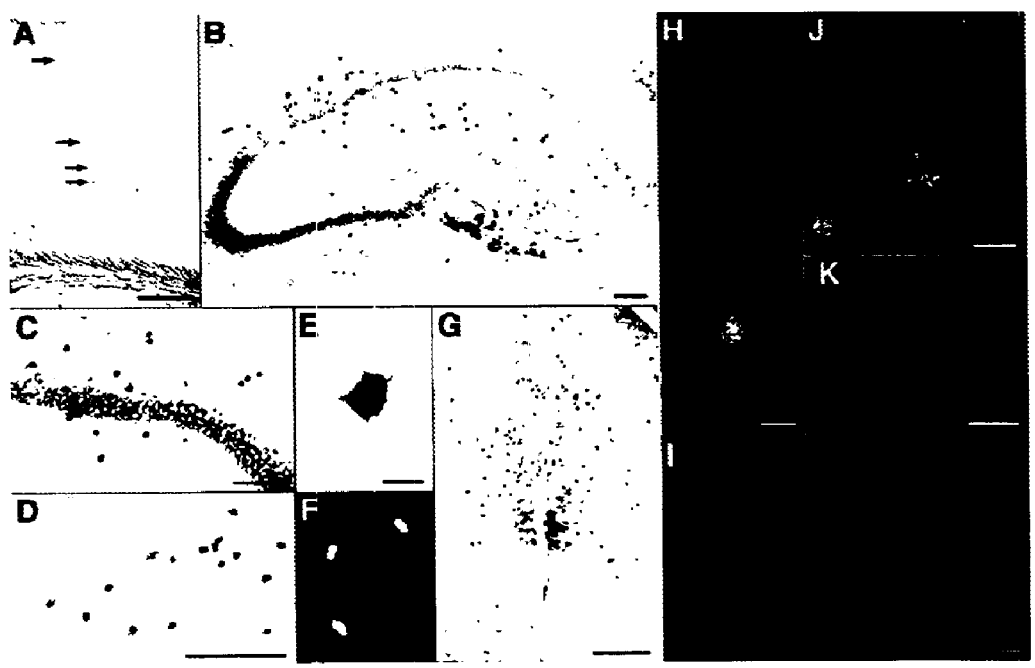

DNA in situ hybridization with a human-specific probe and immunohistochemical detection of a human nucleus-specific antigen revealed the presence of grafted cells in numerous brain regions. Gray matter areas exhibiting widespread donor cell incorporation included cortex (FIG. 3A), hippocampus (FIG. 3B, C), olfactory bulb, septum (FIG. 3D), thalamus, hypothalamus (FIG. 3E), striatum (FIG. 3F) and midbrain (FIG. 3G). Incorporation into white matter regions was most pronounced in the corpus callosum, internal capsule and hippocampal fiber tracts. Morphologically, the incorporated human cells were indistinguishable from the surrounding host cells and only detectable by the use of human-specific markers (FIG. 3). Double labeling with cell type-specific antibodies revealed that the incorporated cells had differentiated into both neurons and glia. Human ES cell-derived neurons could be clearly delineated with antibodies to $\beta_{III}$-tubulin and MAP2 (FIGS. 3H, J). Frequently, they displayed polar morphologies with long processes (FIG. 3H). In addition, neurons with multipolar and immature unipolar morphologies were found (FIG. 3J). The donor-derived neurons generated numerous axons projecting long distances into the host brain, which were detected in both gray and white matter. They were particularly abundant within fiber tracts such as the corpus callosum, the anterior commissure and the fimbria hippocampi where they could frequently be traced for several hundred micrometers within a single section (FIG. 3I).

In addition to neurons, a small number of ES cell-derived astrocytes was detected within the host brain tissue. They displayed stellate morphologies and exhibited strong expression of GFAP (FIG. 3K). In contrast, double labeling of incorporated human cells with antibodies to myelin proteins failed to detect mature oligodendrocytes. Some of the donor cells that had migrated into the host brain retained a nestin-positive phenotype even up to 4 weeks after transplantation. Many of these cells were found in perivascular locations.

Discussion

The present study indicates that engraftable neural precursors capable of generating mature neurons and glia can be generated with high yield from human ES cells. Exploiting growth factor-mediated proliferation/differentiation and differential adhesion of neural precursor cells, the in vitro differentiation procedure described herein provides a new platform for the study of neural development and the generation of donor cells for nervous system repair.

A key finding of this study is the observation that the differentiation of neural precursors from human ES cells appears to recapitulate early steps of nervous system development with the formation of neural tube-like structures in vitro. This phenomenon can now be exploited to study and experimentally manipulate the initial stages of human neural development under controlled conditions. The chemically defined culture system provides a unique opportunity to explore the effects of single factors on human neuroepithelial proliferation and specification in vitro. Similar to precursors derived from the developing human brain, human ES cell-derived precursors show a strong proliferative response to FGF2 (21). However, no additive or synergistic effects on proliferation can be elicited by EGF or LIF. This finding differs from data obtained with primary cells (14, 18–20) and could suggest that proliferating ES cell-derived neural precursors represent a more immature stage than precursor cells derived from the fetal human brain. Studies on rodent cells indeed indicate that neural stem cells isolated from early neurogenesis depend on FGF2 for proliferation and the responsiveness to EGF is acquired only at later stages of neural precursor cell differentiation (22, 23).

The in vitro generation of neural tube-like structures and the possibility to isolate these structures based on their differential adhesion provides a simple yet efficient approach for generating human ES cell-derived neural precursors in high purity. Specifically, the strong cell-cell contacts within the neuroepithelial structures and their low adhesiveness to the tissue culture substrate permits the selective isolation of neural cells without significant contamination of undifferentiated ES cells or cells of other somatic lineages. The high efficiency of this procedure is reflected by the fact that more than 95% of the isolated cells exhibit a nestin-positive phenotype and no ES cells or non-neural epithelia are detectable in transplanted recipients. Since undifferentiated ES cells and precursors to other lineages may form tumors and foreign tissues, the generation of purified somatic cell populations is a key prerequisite for the development of ES cell-based neural transplant strategies.

Following transplantation into the neonatal mouse brain, the ES cell-derived neural precursors incorporated into a large variety of brain regions where they differentiated into neurons and glia. The failure to detect mature oligodendrocytes in vivo is likely due to the low oligodendroglial differentiation efficiency of human neural precursors as opposed to their rodent counterparts (24). Remarkably, donor-derived neurons were not restricted to sites exhibiting postnatal neurogenesis but were also found in many other regions of the brain. Similar data were obtained in studies involving transplantation of human CNS-derived precursors into the adult rodent brain (25). The incorporation of individual precursor cells into postmitotic brain regions is particularly relevant with respect to cell replacement in the adult brain and spinal cord. Yet, more detailed studies will be required to determine whether and to what extent the incorporated cells acquire region-specific properties and become functionally active.

With the exception of intraventricular clusters composed of mature and immature neuroepithelial cells, no space-occupying lesions were detected within the host brains. Most notably, no teratoma formation was observed during a postoperative period up to eight weeks. While it is clear that more rigorous long-term safety studies particularly in non-human primates will be required before considering potential clinical applications, our data indicate that neural precursors isolated from differentiating human ES cells cultures represent a promising donor source for neural repair.

Experimental Protocols

Culture of ES cells. ES cells, H1 (passage 16 to 33), H9 (p34 to 55) and a clonal line derived from H9, H9.2 (p34 to 46) (4) were cultured on a feeder layer of irradiated mouse embryonic fibroblasts with a daily change of a medium that consisted of Dulbecco's modified Eagle's medium (DMEM)/F12, 20% serum replacement (Gibco), 0.1 mM β-mercaptoethanol, 2 µg/ml heparin, and 4 ng/ml of FGF2 (PeproTech Inc., Rochy Hill, N.J.) as previously described (1). Karyotype analysis indicated that the lines at the given passages were diploid.

Differentiation cultures of ES cells. ES cell cultures were incubated with dispase (Gibco BRL, 0.1 mg/ml) at 37° C. for 30 minutes, which removed ES cell colonies intact. The ES cell colonies were pelleted, resuspended in ES cell medium without FGF2, and cultured for 4 days in a 25-cm$^2$ tissue culture flask (Nunc) with a daily medium change. ES cell colonies grew as floating EBs whereas any remaining feeder cells adhered to the flask. The feeder cells were removed by transferring the EBs into a new flask. EBs (~50/flask) were then plated in a 25-cm$^2$ tissue culture flask (Nunc) in DMEM/F12, supplemented with insulin (25 µg/ml), transferrin (100 µg/ml), progesterone (20 nM), putrescine (60 µM), sodium selenite (30 nM), and heparin (2 µg/ml) in the presence of FGF2 (20 ng/ml) (14, 15).

Isolation and culture of neural precursor cells: To separate the clusters of rosette cells from the surrounding flat cells, the cultures were incubated with 0.1 mg/ml dispase at 37° C. for 15–20 minutes. The rosette clumps retracted whereas the surrounding flat cells remained adherent. At this point, the rosette clumps were dislodged by swaying the flask, which left the flat cells adherent. The clumps were pelleted, gently triturated with a 5-ml pipette and plated into a culture flask for 30 minutes to allow the contaminating individual cells to adhere. The floating rosette clumps were then transferred to a new flask coated with poly-(2-hydroxyethyl-methacrylate) to prohibit attachment and cultured in a medium used for human neural precursors (14) with the presence of FGF2 (20 ng/ml). To quantify the efficiency of neural differentiation and isolation, freshly separated cell clusters and the flat cells left behind were dissociated with trypsin (0.025% in 0.1% EDTA) and counted. The percentage of putative neural precursors (rosette cells) among the total cells differentiated from ES cells was obtained based on 3 independent experiments on H9 and H9.2 lines. For analyses of the differentiation potential of the ES cell-derived neural precursors, cells were cultured on ornithine/laminin substrate in a medium consisting of DMEM/F12, N2 supplement (Gibco), cAMP (100 ng/ml), and BDNF (10 ng/ml, PeproTech) without the presence of FGF2. For oligodendrocyte differentiation, the ES cell-derived neural precursors were cultured in DMEM supplemented with N1 (Gibco) and PDGFA (2 ng/ml) as described (14). Morphological observation and immunostaining with markers for precursors and more matured neural cells were performed during the course of differentiation.

Histochemical and immunohistochemical staining. To better visualize the rosette formations, cultures with rosettes were rinsed with PBS and fixed in 4% paraformaldehyde and 0.25% glutardehyde for 1 hour. The fixed cells were then processed for embedding in plastic resin as described (15). The cultured cells were then sectioned in 1-µm thickness and stained with toluidine blue. For immunostaining, the coverslip cultures were immunostained with the following primary antibodies detected by appropriate fluorescent secondary antibodies detailed elsewhere (14, 15): anti-nestin (polyclonal, gift of Dr. R. McKay of NINDS, 1:1,000); anti-polysialylated neuronal cell adhesion molecule (PSA-NCAM, mouse IgM, gift of Dr. G. Rougon of University of Marseille, France, 1:200); anti-Musashi1 (rat IgG, gift of Dr. H. Okano, University of Tokyo, Japan, 1:500); anti-GFAP (polyclonal, Dako, 1:1,000); anti-human GFAP (Sternberg monoclonals, 1:10,000); O4 (mouse IgM, hybridoma supernatant, 1:50); anti-tyrosine hydroxylase (TH, Pel Freez, 1:500). The remaining antibodies were from Sigma: anti-$\beta_{III}$-tubulin (mouse IgG, 1:500); anti-neurofilament (NF) 68 (mouse IgG, 1:1,000); anti-NF 200 (polyclonal, 1:5,000); anti-MAP2ab (mouse IgG, 1:250); anti-$\gamma$-aminobutyric acid (GABA, polyclonal, 1:10,000); anti-glutamate (mouse IgG, 1:10,000). For bromodeoxyuridine (BrdU) incorporation, 4 coverslip cultures in each group were incubated with 2 $\mu$M of BrdU for 16 hours before the cultures were fixed in 4% paraformaldehyde, denatured with 1N HCl and processed for immunolabeling and cell counting (14, 15).

Intracerebroventricular transplantation and in vivo analysis. A suspension of 100,000 viable cells/$\mu$l was prepared in L15 medium (Gibco) after dissociating aggregates of neural precursors with trypsin (0.025% in 0.1% EDTA at 37° C. for 5–10 minutes). Using illumination from below the head, 2~3 $\mu$of cell suspension was slowly injected into each of the lateral ventricles of cryoanesthetized newborn mice (C3HeB/FeJ). The grafted animals were immunosuppressed by daily injection of cyclosporin A (10 mg/kg, i.p.). One, 2, 4, and 8 weeks following transplantation, mice were perfused transcardially with Ringer's followed by 4% paraformaldehyde. Brains were dissected and post-fixed in the same fixative at 4° C. until use. Donor cells were identified in 50-$\mu$m coronal vibratome-sections by in situ hybridization using a digoxigenin-labeled probe to the human alu repeat element (26) or an antibody to a human-specific nuclear antigen (MAB1281, Chemicon, 1:50). Immunopositive cells were double labeled with antibodies to GFAP (1:100), nestin, $\beta_{III}$-tubulin (TUJ1, BabCo, 1:500), MAP2ab (Sigma, clones AP-20 and HM-2, 1:300), and phosphorylated medium molecular weight human neurofilament (clone HO-14, 1:50, a gift of J. Trojanowski). Primary antibodies were detected by appropriate fluorophore-conjugated secondary antibodies. Sections were analyzed on Zeiss Axioskop 2 and Leica laser scan microscopes.

References

1. Thomson, J. A., et al., "Embryonic stem cell lines derived from human blastocysts," Science 282:1145–1147 (1998).
2. Reubinoff, B. E., et al., "Embryonic stem cell lines from human blastocysts: somatic differentiation in vitro," Nat. Biotech. 18:399 (2000).
3. Thomson, J. A. and Odorico, J. S., "Human embryonic stem cell and embryonic germ cell lines," Trends Biotech 18:53–57 (2000).
4. Amit, M., et al., "Clonally derived human embryonic stem cell lines maintain pluripotency and proliferative potential for prolonged periods of culture," Dev. Biol. 227:271–278 (2000).
5. Wiles, M. V. and Keller, G., "Multiple hematopoietic lineages develop from embryonic stem (ES) cells in culture," Development 111:259–267 (1991).
6. Klug, M. G., et al., "Genetically selected cardiomyocytes from differentiating embryonic stem cells form stable intracardiac grafts," J. Clin. Invest. 98:216–224 (1996).
7. Soria, B., et al., "Insulin-secreting cells derived from embryonic stem cells normalize glycemia in streptozotocin-induced diabetic mice," Diabetes 49:157–162 (2000).
8. Bain, G., et al., "Embryonic stem cells express neuronal properties in vitro," Dev. Biol. 168:342–357 (1995).
9. Okabe, S., et al., "Development of neuronal precursor cells and functional postmitotic neurons from embryonic stem cells in vitro," Mech. Dev. 59:89–102 (1996).
10. Mujtaba, T., et al., "Lineage-restricted neural precursors can be isolated from both the mouse neural tube and cultured ES cells," Dev. Biol. 214:113–127 (1999).
11. Brustle, O., et al., "Embryonic stem cell-derived glial precursors: A source of myelinating transplants," Science 285:754–756 (1999).
12. Brustle, O., et al., "In vitro-generated neural precursors participate in mammalian brain development," Proc. Natl. Acad. Sci. USA 94:14809–14814 (1997).
13. McDonald, J. W., et al., "Transplanted embryonic stem cells survive, differentiate and promote recovery in injured rat spinal cord," Nat. Med. 5:1410–1412 (1999).
14. Zhang, S.-C., et al., "Tracing human oligodendroglial development in vitro," J. Neurosci. Res. 59:421–429 (2000).
15. Zhang, S.-C., et al., "Adult brain retains the potential to generate oligodendroglial progenitors with extensive myelination capacity," Proc. Natl. Acad. Sci. USA 96:4089–4094 (1999).
16. Lendahl, U., et al., "CNS stem cells express a new class of intermediate filament protein," Cell 60:585–595 (1990).
17. Kaneko, Y., et al., "Musashi1: An evolutionarily conserved marker for CNS progenitor cells including neural stem cells," Dev. Neurosci. 22:139–153 (2000).
18. Svendsen, C. N., et al., "Survival and differentiation of rat and human epidermal growth factor-responsive precursor cells following grafting into the lesioned adult central nervous system," Exp. Neurol. 137:376–388 (1996).
19. Carpenter, M. K., et al., "In vitro expansion of a multipotent population of human neural progenitor cells," Exp. Neurol. 158:265–278 (1999).
20. Vescovi, A. L., et al., "Isolation and cloning of multipotential stem cells from the embryonic human CNS and establishment of transplantable human neural stem cell lines by epigenetic stimulation," Exp. Neurol. 156:71–83 (1999).
21. Flax, J. D., et al., "Engraftable human neural stem cells respond to developmental cues, replace neurons, and express foreign genes," Nat. Biotech. 16:1033–1039 (1998).
22. Kalyani, A. D., et al., "Neuroepithelial stem cells from the embryonic spinal cord: isolation, characterization and clonal analysis," Dev. Biol. 186:202–223 (1997).
23. Fricker, R. A., et al., "Site-specific migration and neuronal differentiation of human neural progenitor cells after transplantation in the adult rat brain," J. Neurosci. 19:5990–6005 (1999).
24. Svendsen, C. N., et al., "Human neural stem cells: Isolation, expansion and transplantation," Brain Pathol. 9:499–513 (1999).
25. Tropepe, V., et al., "Distinct neural stem cells proliferate in response to EGF and FGF in the developing mouse telencephalon," Dev. Biol. 208:166–188 (1999).
26. Brustle, O., et al., "Chimeric brains generated by intraventricular transplantation with human brain cells into embryonic rats," Nat. Biotech. 16:1040–1044 (1998).

We claim:

1. A method of differentiating primate embryonic stem cells into neural precursor cells, comprising the steps of:

(a) obtaining a primate embryonic stem cell culture,
(b) propagating the stem cells, wherein embryoid bodies are formed, and
(c) culturing the embryoid bodies in a medium consisting essentially of DMEM/F12, insulin, transferrin, progesterone, putrescine, sodium selenite, heparin and an effective amount of fibroblast growth factor 2, wherein neural precursor cells are generated and wherein the neural precursor cells form rosette formations.

* * * * *